United States Patent
Hauner-Westphal et al.

(10) Patent No.: US 12,186,143 B2
(45) Date of Patent: Jan. 7, 2025

(54) METHOD FOR EXCAVATING DENTAL MATERIAL

(71) Applicant: Ivoclar Vivadent AG, Schaan (LI)

(72) Inventors: Martina Hauner-Westphal, Feldkirch (AT); Arnd Peschke, Planken (LI); Thorsten Bock, Feldkirch (AT)

(73) Assignee: Ivoclar Vivadent AG, Schaan (LI)

(*) Notice: Subject to any disclaimer, the term of this patent is extended or adjusted under 35 U.S.C. 154(b) by 36 days.

(21) Appl. No.: 17/552,837

(22) Filed: Dec. 16, 2021

(65) Prior Publication Data

US 2022/0192782 A1 Jun. 23, 2022

(30) Foreign Application Priority Data

Dec. 21, 2020 (EP) .................................. 20215895

(51) Int. Cl.
*A61C 1/00* (2006.01)
*A61B 7/02* (2006.01)

(52) U.S. Cl.
CPC ............ *A61C 1/0007* (2013.01); *A61B 7/023* (2013.01); *A61C 1/0061* (2013.01)

(58) Field of Classification Search
CPC ....... A61C 1/0046; A61C 1/00; A61C 1/0007; A61C 1/0061; A61C 1/0084; A61C 17/0202; A61C 3/02; A61C 3/025; A61C 5/40; A61C 5/42; A61C 5/44; A61C 19/042; A61C 19/043; A61C 17/20
See application file for complete search history.

(56) References Cited

U.S. PATENT DOCUMENTS

| | | | | |
|---|---|---|---|---|
| 5,501,599 A | * | 3/1996 | Rechmann | A61C 1/0046 433/215 |
| 5,795,153 A | * | 8/1998 | Rechmann | A61C 1/0046 433/215 |
| 8,326,413 B1 | * | 12/2012 | McClain | A61B 5/4547 433/167 |
| 8,734,153 B2 | * | 5/2014 | Arzanpour | A61C 1/0007 433/131 |
| 9,133,839 B2 | * | 9/2015 | Rampen | F04B 53/1082 |
| 9,333,060 B2 | | 5/2016 | Hunter | |
| 9,504,536 B2 | | 11/2016 | Bergheim et al. | |
| 9,675,426 B2 | * | 6/2017 | Bergheim | A61C 5/40 |
| 10,420,630 B2 | * | 9/2019 | Bergheim | A61C 5/40 |
| 10,722,325 B2 | * | 7/2020 | Khakpour | A61C 3/02 |
| 11,160,645 B2 | | 11/2021 | Bergheim et al. | |
| 2004/0226346 A1 | | 11/2004 | Schluecker et al. | |
| 2005/0091770 A1 | * | 5/2005 | Mourad | A46B 15/0028 15/22.1 |
| 2006/0195072 A1 | * | 8/2006 | Miller | B23K 26/36 606/2 |

(Continued)

FOREIGN PATENT DOCUMENTS

WO 2011/107117 A1 9/2011

*Primary Examiner* — Heidi M Eide
(74) *Attorney, Agent, or Firm* — Ann M. Knab; Thad McMurray

(57) ABSTRACT

A method for excavating tooth material, having the steps of placing (S101) a structure-borne sound sensor on a tooth; excavating (S102) the tooth material by means of a fluid jet; detecting (S103) structure-borne sound signals during excavation by the structure-borne sound sensor; and regulating or controlling (S104) a fluid jet generating device based on the structure-borne sound signals.

10 Claims, 8 Drawing Sheets

(56) References Cited

U.S. PATENT DOCUMENTS

| | | | |
|---|---|---|---|
| 2010/0143861 A1* | 6/2010 | Gharib | A61C 19/04 433/81 |
| 2010/0227295 A1* | 9/2010 | Maev | A61B 8/0875 433/215 |
| 2011/0107117 A1 | 5/2011 | Jung et al. | |
| 2011/0117517 A1* | 5/2011 | Bergheim | A61C 5/40 433/81 |
| 2011/0311939 A1* | 12/2011 | Hunter | A61C 17/024 433/80 |
| 2012/0237893 A1* | 9/2012 | Bergheim | A61C 5/44 433/81 |
| 2014/0099597 A1* | 4/2014 | Bergheim | A61C 17/0208 433/119 |
| 2015/0044632 A1 | 2/2015 | Bergheim et al. | |
| 2015/0140503 A1* | 5/2015 | Bergheim | A61C 17/02 433/80 |
| 2015/0147718 A1* | 5/2015 | Khakpour | A61C 5/62 433/81 |
| 2015/0173852 A1* | 6/2015 | Khakpour | A61C 1/0046 433/215 |
| 2015/0305627 A1* | 10/2015 | Islam | G01N 21/35 433/29 |
| 2015/0305670 A1* | 10/2015 | Spruit | A61B 5/0088 433/27 |
| 2015/0327952 A1* | 11/2015 | Boehm | A61C 1/12 433/88 |
| 2015/0342618 A1* | 12/2015 | Nguyen | A61C 8/0092 433/27 |
| 2016/0095679 A1* | 4/2016 | Khakpour | A61C 17/0208 433/81 |
| 2017/0202637 A1* | 7/2017 | Ahmadi | A61B 5/746 |
| 2017/0281312 A1* | 10/2017 | Khakpour | A61C 17/024 |
| 2018/0214247 A1* | 8/2018 | Sharma | A61C 5/50 |
| 2020/0139146 A1* | 5/2020 | Khakpour | A61C 17/20 |
| 2021/0255147 A1 | 8/2021 | Ryu et al. | |
| 2021/0279573 A1 | 9/2021 | Tnani et al. | |
| 2021/0293354 A1 | 9/2021 | Sprakel et al. | |
| 2021/0346678 A1 | 11/2021 | Baumbach et al. | |

\* cited by examiner

METHOD FOR EXCAVATING DENTAL MATERIAL

CROSS-REFERENCE TO RELATED APPLICATIONS

This application claims priority to European Patent Application No. 20215895.2 filed on Dec. 21, 2020, the disclosure of which is incorporated herein by reference in its entirety.

TECHNICAL FIELD

The present invention relates to a method for excavating dental material and a system for excavating dental material.

BACKGROUND

During excavation, i.e. the removal of carious tooth material from a tooth by means of a high-pressure fluid jet, it can happen that too much tooth material is unintentionally removed. This may even result in pulp perforation, which irreversibly damages the nerve of the tooth.

SUMMARY

It is therefore the technical task of the present invention to prevent unwanted removal of tooth material during an excavation process by means of a fluid jet.

This task is solved by objects according to the independent claims. Technically advantageous embodiments are the subject of the dependent claims, the description and the drawings.

According to a first aspect, the technical problem is solved by a method for excavating tooth material, comprising the steps of placing a structure-borne sound sensor on a tooth; excavating the tooth material by means of a high-pressure fluid jet; detecting structure-borne sound signals during excavation by the structure-borne sound sensor; and regulating or controlling a fluid jet generating device based on the structure-borne sound signals. Through feedback via the structure-borne sound signals, differences in the hard tissue of the tooth can be detected. In this way, for example, the quality of the fluid jet can be adapted to the area that is currently being processed by the fluid jet. In addition, the fluid jet can be automatically deactivated when it encounters a specific material. Pulp perforation can be prevented in this way.

Examples of sensors are set forth in US 20210346678, 20210293354, 20210279573, 20210255147, 20210293354, and 20040226346, which are hereby incorporated by reference in their entirety.

U.S. Pat. Nos. 5,795,153, 11,160,645, 9,333,060, 9,504,536, U.S. 20150044632 and 20110107117 are directed to devices/methods for removing deposits from teeth and are hereby incorporated by reference in their entirety.

In a technically advantageous embodiment of the method, the fluid jet is deactivated in response to the structure-borne sound signals. This has, for example, the technical advantage of preventing unwanted and excessive removal of tooth material.

In a further technically advantageous embodiment of the method, a continuous or a pulsed fluid jet is generated in response to the structure-borne sound signals. This has the technical advantage, for example, that the method characteristics of the fluid jet can be adjusted to the type of tooth material.

In a further technically advantageous embodiment of the method, a pressure of the fluid jet generation is regulated or controlled in response to the structure-borne sound signals. This has, for example, the technical advantage that the pressure of the fluid jet can be adjusted to the type of tooth material.

In a further technically advantageous embodiment of the method, the type of tooth material is detected based on a slope of a cumulative energy of bursts. This has the technical advantage, for example, that the type of tooth material can be reliably detected based on the slope values.

In a further technically advantageous embodiment of the method, the type of tooth material is detected based on a number of bursts per time unit. This also has the technical advantage, for example, that the type of tooth material can be detected quickly and reliably.

In a further technically advantageous embodiment of the method, carious tooth material is detected based on the frequencies of the bursts. This also has the technical advantage, for example, that tooth material to be removed can be identified with a high degree of accuracy.

In a further technically advantageous embodiment of the method, the fluid jet is deactivated when carious tooth material is no longer detected. This also has the technical advantage, for example, that only carious tooth material is removed.

In a further technically advantageous embodiment of the method, the structure-borne sound signals are detected at a sampling rate of up to 1 MHz. This also has the technical advantage, for example, that a broad data basis can be obtained for the acquisition of structure-borne sound signals for controlling the fluid jet.

According to a second aspect, the technical problem is solved by a system for excavating tooth material, comprising a structure-borne sound sensor for detecting structure-borne sound signals during excavation; a fluid jet generating device for generating a fluid jet for excavating the tooth material; and a device for regulating or controlling the fluid jet generating device based on the structure-borne sound signals. An evaluation unit is capable of determining and evaluating individual bursts in the structure-borne sound signals. The evaluation unit is able to determine the frequency and the energy of the bursts. The system has the same technical advantages as the method according to the first aspect.

In a further technically advantageous embodiment of the system, the system is designed to regulate or control the fluid jet generation device in such a way that the fluid jet is deactivated in response to the structure-borne sound signals, a continuous or a pulsed fluid jet is generated in response to the structure-borne sound signals, and/or the pressure of the fluid jet generation is regulated or controlled in response to the structure-borne sound signals. This also has the technical advantage, for example, that the process characteristics of the fluid jet can be adjusted to the type of tooth material.

In a further technically advantageous embodiment of the system, the device is designed to recognize the type of tooth material based on a slope of a cumulative energy of bursts. This also has, for example, the technical advantage that the type of tooth material can be reliably detected.

In a further technically advantageous embodiment of the system, the device is designed to recognize the type of tooth material based on a number of bursts per unit of time. This also has the technical advantage, for example, that the type of tooth material can be reliably detected.

In a further technically advantageous embodiment of the system, the device is designed to detect carious tooth material based on a frequency of bursts. This has, for example, the technical advantage that the fluid jet can only be used to remove carious tooth material.

In a technically advantageous embodiment of the system, an evaluation unit of the structure-borne sound sensor has a sampling rate of up to 1 MHz. This also has the technical advantage, for example, that a broad data basis can be obtained for the acquisition of structure-borne sound signals for regulating or controlling the fluid jet.

BRIEF DESCRIPTION OF THE DRAWINGS

Examples of embodiments of the invention are shown in the drawings and are described in more detail below. The drawings show.

DETAILED DESCRIPTION

Figure 1:
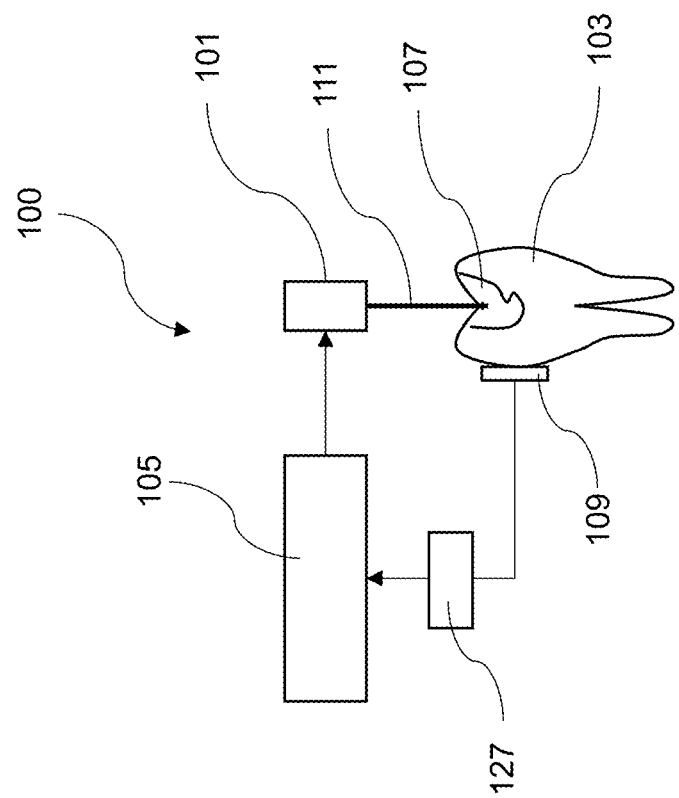
FIG. 1 a schematic view of a system for excavating tooth material.

FIG. 1 shows a schematic view of a system 100 for excavating tooth material 107. The system 100 comprises a fluid jet generating device 101 for generating a fluid jet 111 for excavating tooth material 107 of tooth 103. The fluid jet is, for example, a water jet or a jet of sodium chloride or also Ringer's solution. A structure-borne sound sensor 109 is used to detect structure-borne sound signals during the process of excavating. For this purpose, the structure-borne sound sensor 109 is coupled to the tooth 103 in such a way that it can detect the structure-borne sound waves of the tooth 103 generated by the fluid jet 111. The structure-borne sound signals thus collected are amplified by means of the evaluation unit 127, evaluated and transmitted electronically to an electronic device 105 for closed-loop or open-loop control with a microprocessor. This device 105 evaluates the information from the evaluation unit 127 and controls the fluid jet generation device 101 based on these obtained characteristics. A closed control loop for the fluid jet 111 is thereby implemented.

Differences in the hard tissue of tooth 103 can be detected by evaluating the structure-borne sound signals. For example, it can be determined based on the structure-borne sound signals whether an enamel area, a dentin area or a carious area of tooth 103 is being processed by means of the fluid jet 111.

The fluid jet 111 generated at a pressure of 1 to 500 bar in a nozzle of the fluid jet generation device 101 has, for example, a jet diameter of 0.08 to 0.3 mm. The fluid jet 111 may emerge as a continuous jet or as a pulsating jet. Depending on the frequency, the pulsating fluid jet 111 can be built up from 20 to 40000 separate droplets or fluid packets per second during pulse excitation. This corresponds to a droplet frequency of 20 Hz to 40 kHz.

The fluid jet generation device 101 may be electronically regulated or controlled, for example, to change the pressure of the fluid jet generation device 111 or to selectively turn the fluid jet 111 on or off. In addition, the fluid jet generation device 101 may be regulated or controlled such that it generates a continuous fluid jet 111 or a pulsating fluid jet 111 or changes the fluid jet generation pressure. To this end, the fluid jet generating device 101 is coupled to the device 105.

The structure-borne sound sensor 109 is an active or passive sensor and is attached to the tooth where the excavation of the tooth material 107 is performed. The structure-borne sound can also be transmitted via the jaw to another tooth or the jaw itself and is measured there. The structure-borne sound sensor 109 is capable of detecting the transmitted sound signals of the tooth 103 in the structure-borne sound range during the excavation by means of the fluid jet 111. For example, the evaluation unit 127 operates at a sampling rate of 1 MHz, so that structure-borne sound signals of the tooth 103 can be detected up to a frequency of 500 kHz. In general, however, the structure-borne sound sensor 109 with associated evaluation unit 127 can also be designed to measure signals in other frequency ranges.

The electrical structure-borne sound signals of the structure-borne sound sensor 109 can be amplified by an electronic amplifier so that they can be better evaluated by the evaluation unit 127 and further processed in the device 105. The amplifier and/or the evaluation unit 127 may additionally comprise an analog-to-digital converter, so that the measured values obtained can be transmitted directly to and processed by the digital device 105. For this purpose, a computer program can be executed by the evaluation unit 127 and/or device 105, or the control unit 105 comprises a suitable evaluation unit itself.

Figure 2:
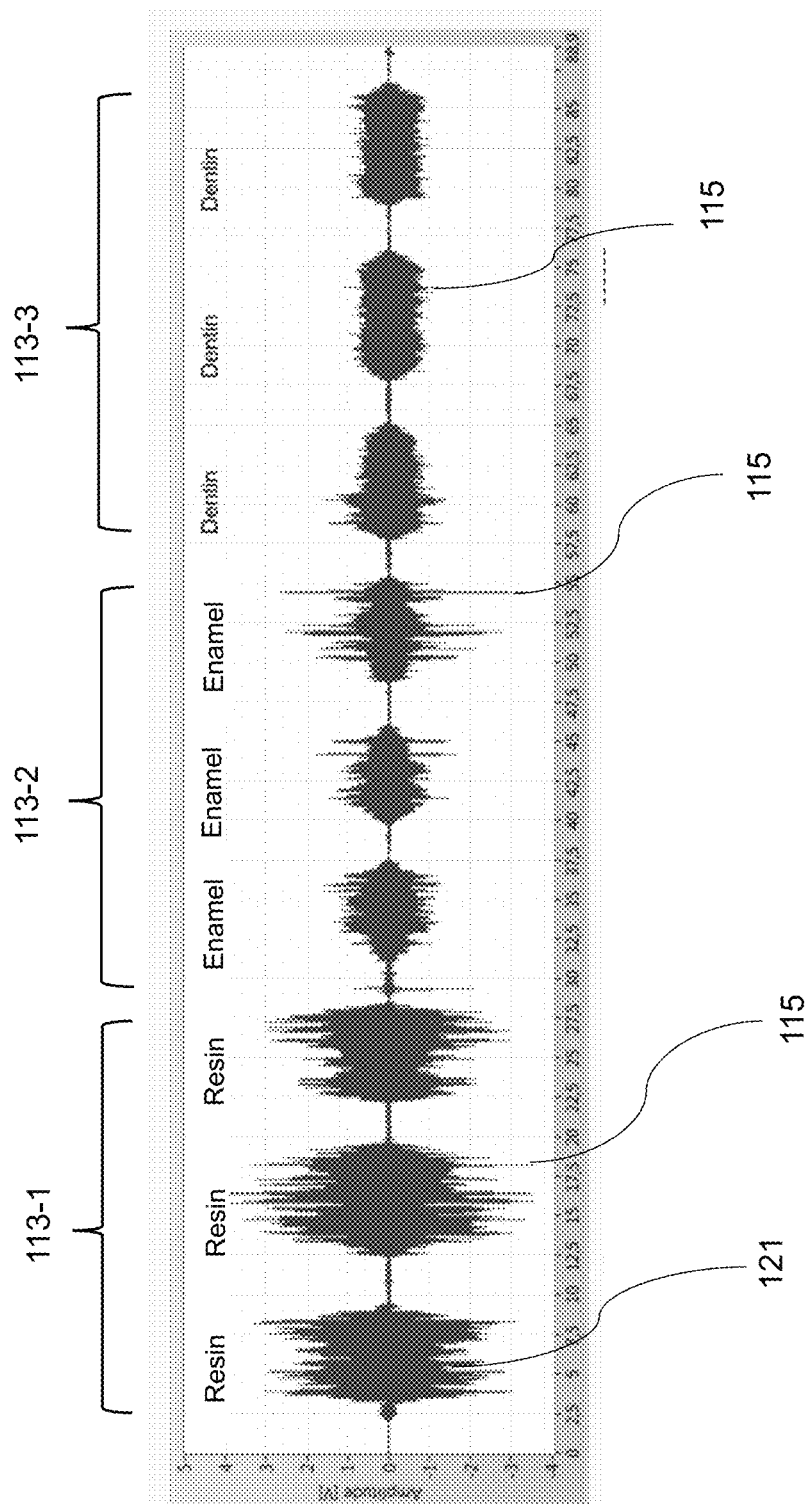
FIG. 2 an exemplary diagram of structure-borne sound signals.

FIG. 2 shows an exemplary diagram of structure-borne sound signals 121 obtained by the structure-borne sound sensor 109 during processing of a tooth sample in different tooth regions. The diagram shows the detected amplitude of the structure-borne sound signals 121 as a function of time or samples obtained in three different time ranges 113-1, . . . , 113-3.

In the first time zone 113-1, the fluid jet 111 generated at a pressure of 250 bar impinges on a resin region of the embedded tooth sample. In time zone 113-2, the same fluid jet 111 impinges on an enamel region of tooth 103, and in time zone 113-3, the same fluid jet 111 impinges on a dentin region of tooth 103.

The structure-borne sound signals 121 differ depending on the material on which the fluid jet 111 impinges. Therefore, different amplitude peaks (so-called bursts) 115 occur in each time range 113-1, . . . , 113-3, from which conclusions can be drawn about the type and degree of hardness of the machined tooth material 107. A burst 115 occurs when tooth material 107 is ablated by the fluid jet 111 and causes a clank or crackle in the structure-borne sound range. A burst 115 is represented as a peak in the signal-time diagram. By means of a structure-borne sound measurement and the digital evaluation of the resulting short-time bursts 115, it is possible to distinguish between the different tooth hard substances, such as different tooth materials or filling materials. This in turn can be used for regulation or control of the fluid jet 111.

Figure 3:
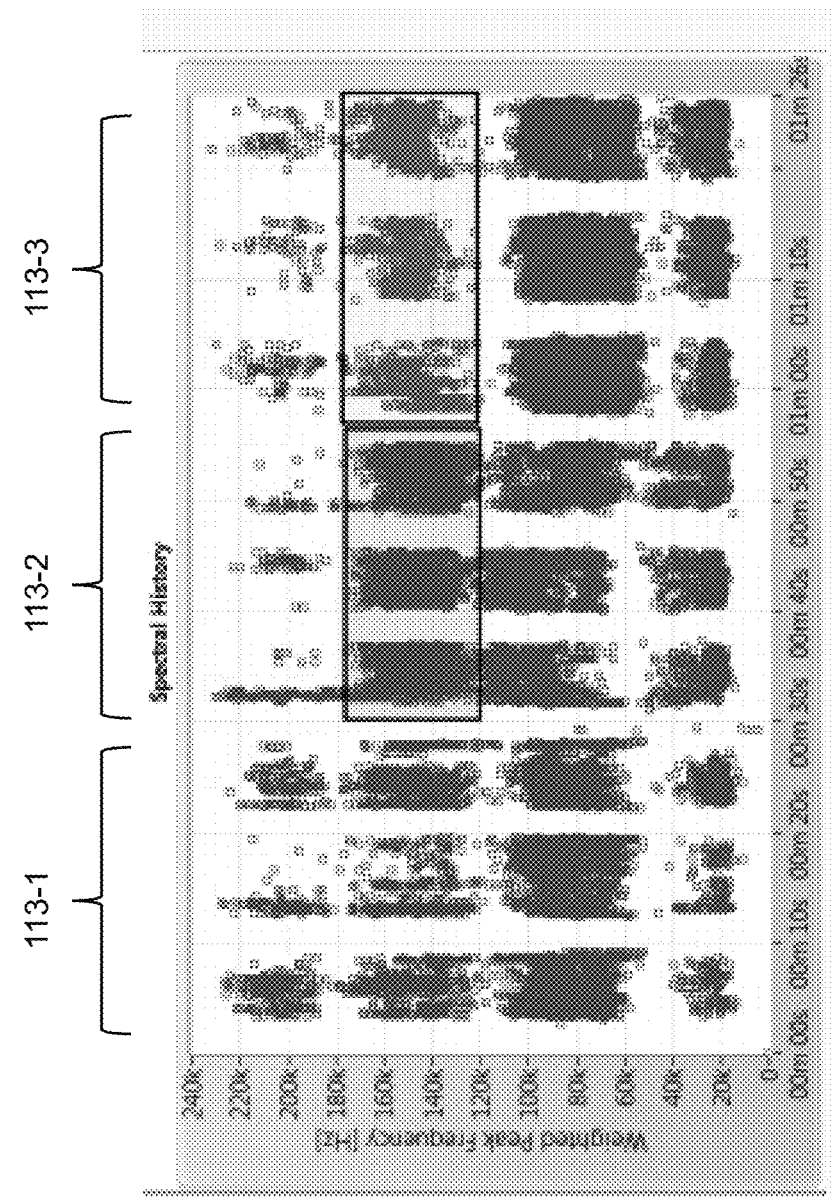
FIG. 3 a diagram for evaluating the structure-borne sound signals.

FIG. 3 shows a diagram for evaluating the structure-borne sound signals 121. In this diagram, the weighted frequency of all bursts 115 obtained over time during processing of the sample by means of the fluid jet 111 in the different time ranges 113-1, . . . , 113-3 is shown. The weighted frequency of the bursts 115 that occur can be obtained, for example, from the time-dependent structure-borne sound signal 121 using a Fourier analysis. The weighting can be done based on the center of gravity of the frequency spectrum.

In each time range 113-1, . . . , 113-3, a different distribution of the weighted frequencies of the bursts 115 occurs depending on which type of tooth material 107 is currently being struck by the fluid jet 111.

Figure 4:
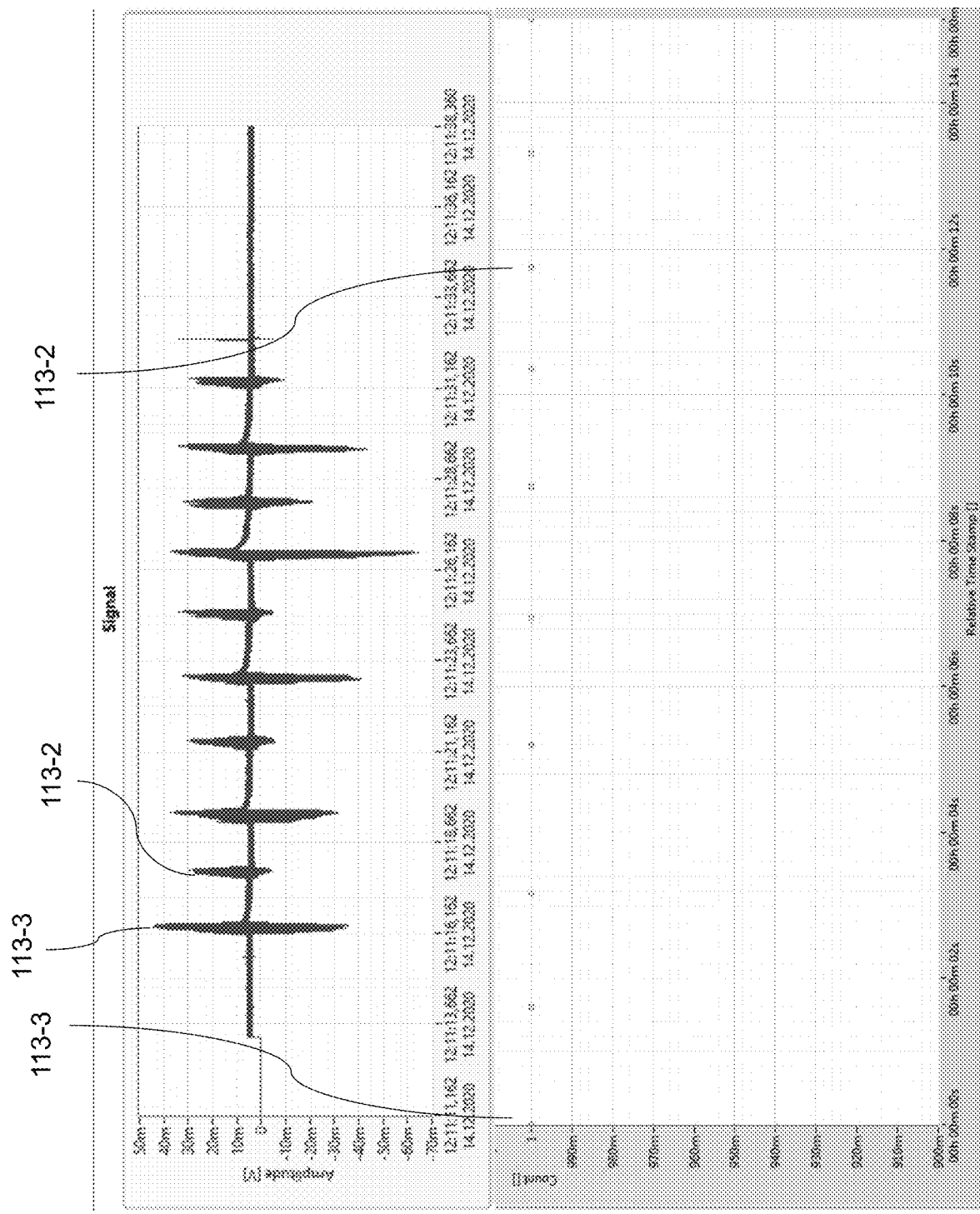
FIG. 4 a further diagram for the evaluation of the structure-borne sound signals.

FIG. 4 shows another diagram for the evaluation and clustering of the structure-borne sound signals, in which dentin 113-3 and enamel 113-2 are processed. In the dentin, the signal amplitude is higher than in the enamel area of the tooth. After clustering the bursts, e.g. on the basis of the selected parameters like partial power, weighted peak frequency, frequency centroid energy and peak signal, a clear distinction can be made between dentin 113-3 (circles) and enamel 113-2 (circles).

Figure 5:
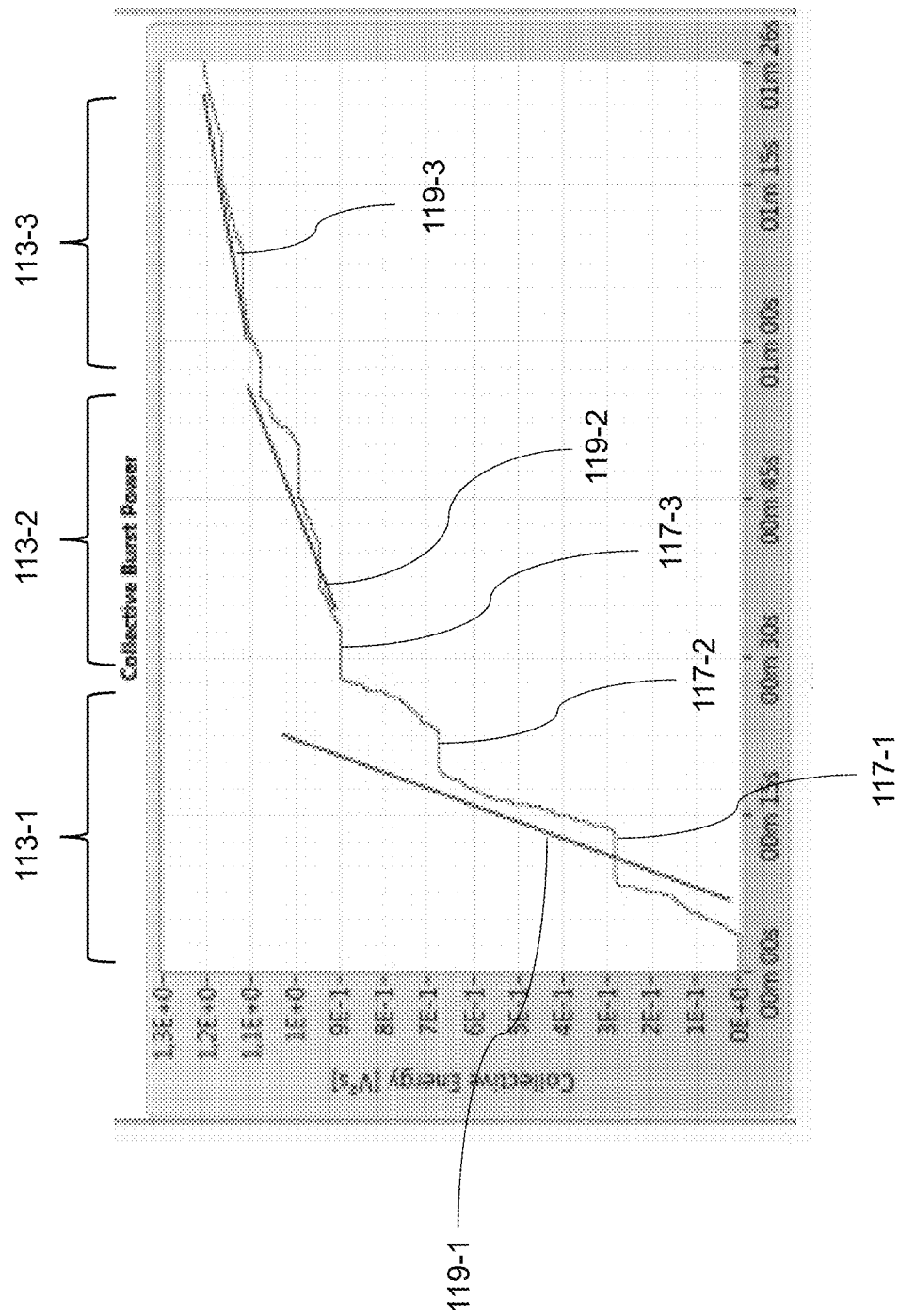
FIG. 5 a further diagram for the evaluation of the structure-borne sound signals.

FIG. 5 shows another diagram for evaluating the structure-borne sound signals 121. In this diagram, the cumulative energy of the bursts 115 over time is shown. In the area 113-1, in which the fluid jet 111 impinges on the resin area of the embedded tooth sample, the cumulative energy of the bursts 115 has a different slope per unit of time than in the area 113-2, in which the fluid jet 111 impinges on an enamel area of the tooth 103 or in the area 113-3, in which the fluid jet 111 impinges on a dentin area of the tooth 103. Depending on the slope in diagram 119-1, . . . , 119-3 of the cumulative energy of the bursts 115, it is therefore possible to determine which type of tooth material of tooth 103 is currently being processed by fluid jet 111. In the horizontal areas 117-1, . . . , 117-3, no machining takes place by the fluid jet 111. The cumulative energy of the bursts 115 therefore does not increase in these time ranges.

Figure 6:
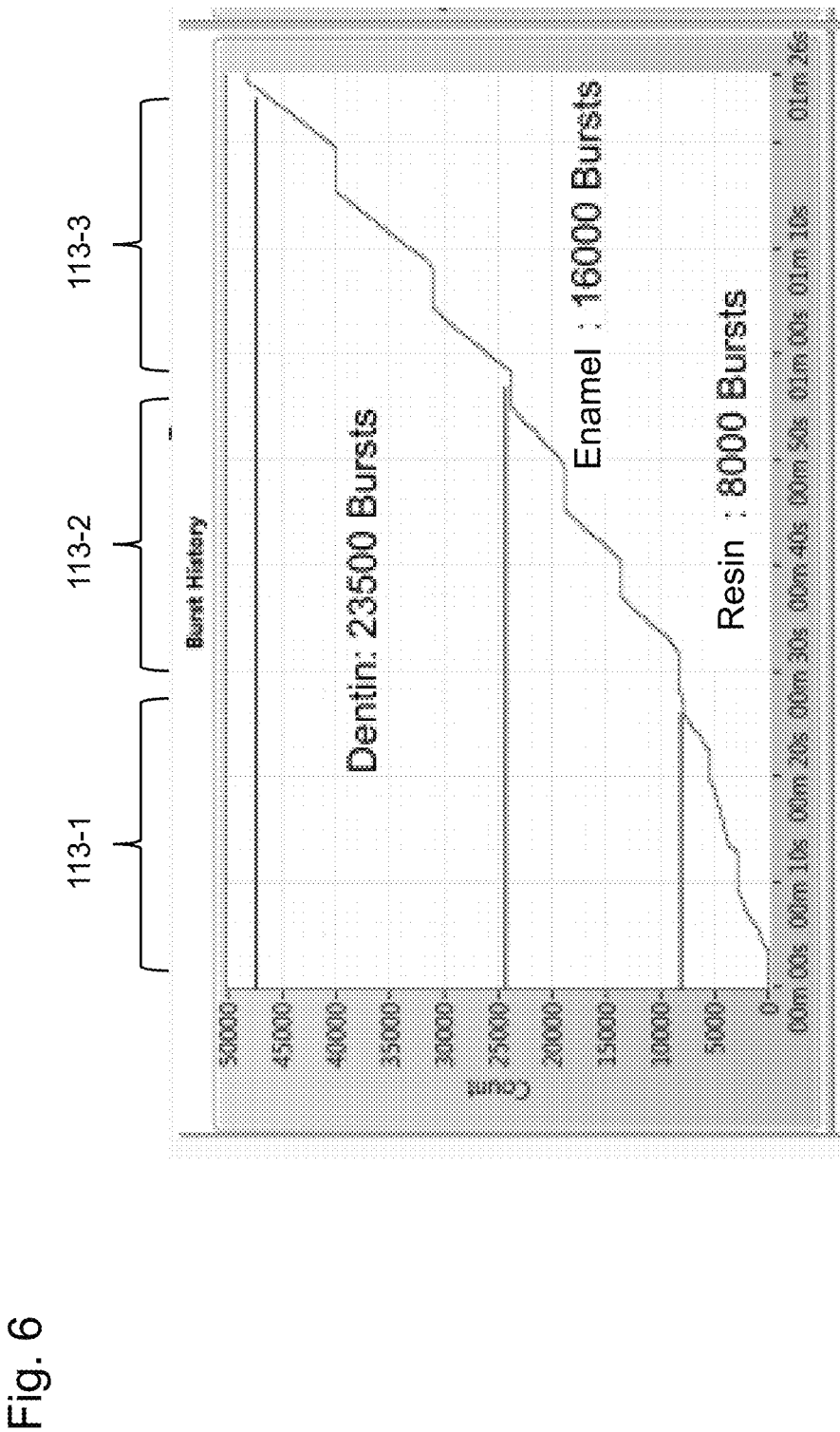
FIG. 6 a further diagram for the evaluation of the structure-borne sound signals.

FIG. 6 shows another diagram for evaluating the structure-borne sound signals 121. In this diagram, the cumulative number of bursts 115 is plotted as a function of time. When machining the synthetic resin in the time range 113-1, 8,000 bursts are counted. When machining the enamel area in time range 113-2, 16,000 bursts are counted and when machining in time range 113-3, 23,500 bursts are counted. Based on the number of bursts 115 per time unit, it is therefore possible to determine which type of tooth material is involved. Based on the number of bursts per unit time, it can be determined what type of tooth material 107 is being impacted by the fluid jet 111.

Figure 7:
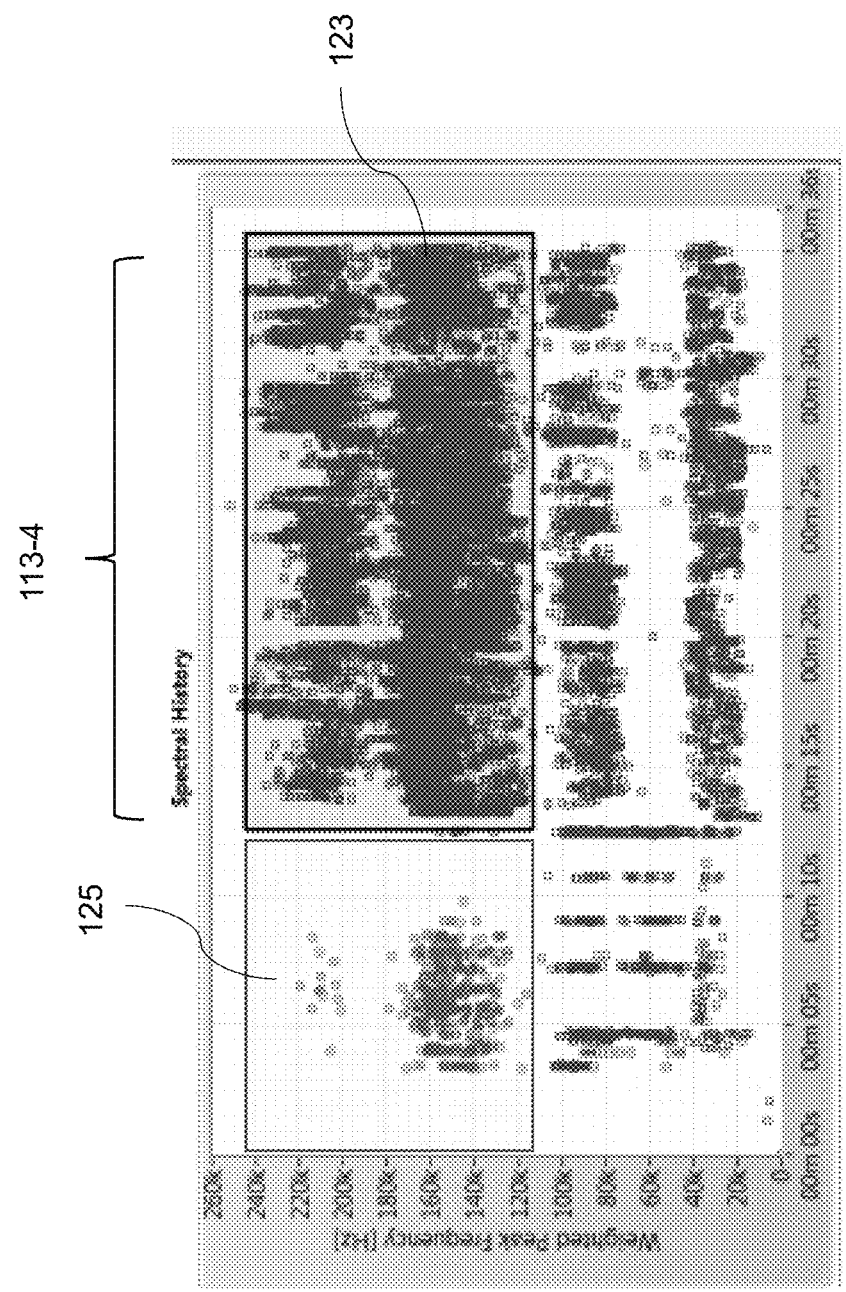
FIG. 7 a further diagram for evaluating the structure-borne sound signals of carious tooth material.

FIG. 7 shows another diagram for evaluating the structure-borne sound signals 121 from carious tooth material 107. This diagram also shows the weighted frequency of all bursts 115 obtained over time when the tooth 103 is processed by the fluid jet 111. If the fluid jet 111 encounters a carious tooth material 107 in the area 113-4, more bursts with higher weighted frequencies occur in the area 123. In contrast, fewer bursts with higher weighted frequencies occur in region 125 for healthy tooth material.

By evaluating the structure-borne sound signals 121, the processing of carious tooth material 107 can thus also be detected. In this case, increased burst formation occurs in the upper frequency range. This can be used to perform the processing with the fluid jet 111 only until the carious tooth material 107 has been removed. As soon as the fluid jet 111 encounters healthy tooth material 107, the frequencies of the bursts 115 shift to the lower frequency range. In this case, the fluid jet 111 can be automatically deactivated. This prevents the removal of healthy tooth material 107 as far as possible.

Figure 8:
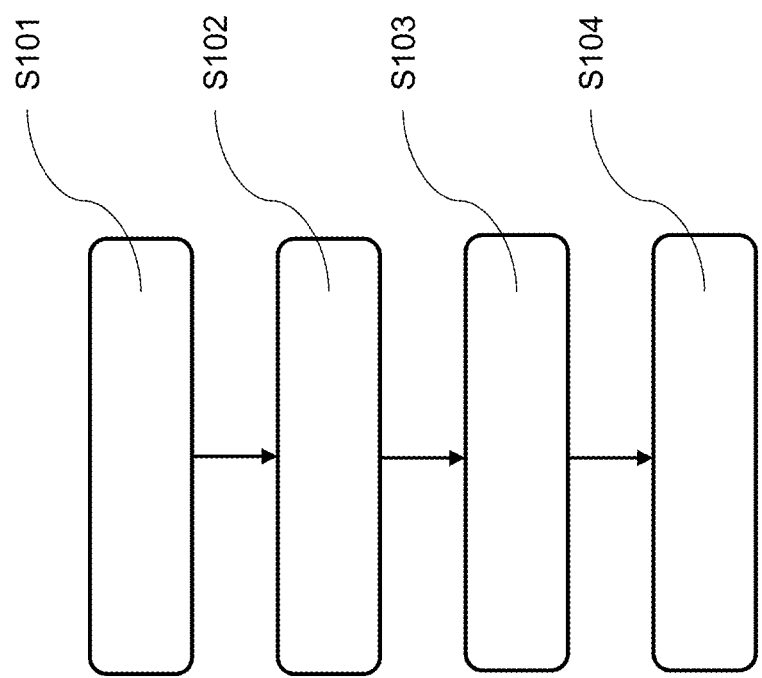
FIG. 8 a block diagram of a method for excavating tooth material.

FIG. 8 shows a block diagram of a method for excavating tooth material 107. First, in step S101, a structure-borne sound sensor 109 is attached to tooth 103. In step S102, the tooth material 107 is removed (excavated) by means of the fluid jet 111. Simultaneously, in step S103, the structure-borne sound signals 121 are detected by the structure-borne sound sensor 109 during the excavation. The structure-borne sound signals 121 can additionally be amplified and evaluated. Thereafter, in step S104, the fluid jet generating device 101 is regulated or controlled based on the structure-borne sound signals 121.

For the regulation or control of the fluid jet generation device 101, the time-varying burst development (counts) as well as their time-varying energy development (summation) and their frequency position are considered in addition to the time signal of the structure-borne sound signals 121. The evaluation unit 127 is capable of autonomously determining the frequency, the energy and/or the number of bursts 115.

This method makes it possible to identify which material is currently being processed by the fluid jet 111. Depending on the material, the fluid jet generating device 101 can then modify the properties of the fluid jet 111 or deactivate it completely. In this way, an unintentional excavation of tooth material 107 or a powder shot can be avoided.

All features explained and shown in connection with individual embodiments of the invention may be provided in different combinations in the subject matter of the invention to simultaneously realize their beneficial effects.

All method steps can be implemented by devices which are suitable for executing the respective method step. All functions that are executed by the features in question can be a method step of a method.

In some embodiments, the innovations may be implemented in diverse general-purpose or special-purpose computing systems. For example, the computing environment can be any of a variety of computing devices (e.g., desktop computer, laptop computer, server computer, tablet computer, gaming system, mobile device, programmable automation controller, etc.) that can be incorporated into a computing system comprising one or more computing devices.

In some embodiments, the computing environment includes one or more processing units and memory. The processing unit(s) execute computer-executable instructions. A processing unit can be a central processing unit (CPU), a processor in an application-specific integrated circuit (ASIC), or any other type of processor. In a multi-processing system, multiple processing units execute computer-executable instructions to increase processing power. A tangible memory may be volatile memory (e.g., registers, cache, RAM), non-volatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage, one or more input devices, one or more output devices, and one or more communication connections. An interconnection mechanism such as a bus, controller, or network, interconnects the components of the computing environment. Typically, operating system software provides an operating environment for other software executing in the computing environment, and coordinates activities of the components of the computing environment.

The tangible storage may be removable or non-removable, and includes magnetic or optical media such as magnetic disks, magnetic tapes or cassettes, CD-ROMs, DVDs, or any other medium that can be used to store information in a non-transitory way and can be accessed within the computing environment. The storage stores instructions for the software implementing one or more innovations described herein.

The input device(s) may be, for example: a touch input device, such as a keyboard, mouse, pen, or trackball; a voice input device; a scanning device; any of various sensors; another device that provides input to the computing environment; or combinations thereof. The output device may be a display, printer, speaker, CD-writer, or another device that provides output from the computing environment.

The scope of protection of the present invention is given by the claims and is not limited by the features explained in the description or shown in the figures.

REFERENCE LIST

100 System for excavating dental material
101 Fluid jet generating device or Fluid jet generator
103 Tooth
105 Regulator or Controller
107 Dental material
109 Structure-borne sound sensor
111 Fluid jet
113 Time range
115 Bursts
117 Area
119 Range
121 Structure-borne sound signals
123 Area of carious tooth material
125 Healthy dental material area
127 Evaluator or Evaluation unit

The invention claimed is:

1. A method for excavating dental material (107) comprising:
   arranging (S101) a structure-borne sound sensor (109) on a tooth (103);
   excavating (S102) the tooth material (107) comprising carious tooth material with a fluid jet (111);
   detecting (S103) structure-borne sound signals (121) of the tooth (103), generated by the fluid jet (111) during the excavation, by the structure-borne sound sensor (109); and
   regulating or controlling (S104) a fluid jet generator (101), which controls the fluid jet, based on the structure-borne sound signals (121);
   wherein a type of tooth material is detected based on the structure-borne sound signals;
   wherein the type of tooth material (107) is detected based on a slope of a cumulative energy of bursts (115) and the frequency of the bursts or the number of bursts per unit of time.

2. The method of claim 1, wherein the fluid jet (111) is deactivated in response to the structure-borne sound signals (121).

3. The method of claim 1, wherein the fluid jet (111) is a continuous or a pulsed fluid jet (111) that is generated in response to the structure-borne sound signals (121).

4. The method of claim 1, wherein a pressure of the fluid jet generation is regulated or controlled in dependence on the structure-borne sound signals (121).

5. The method of claim 1, wherein the fluid jet (111) is deactivated when the carious tooth material (107) is no longer detected.

6. The method of claim 1, wherein the structure-borne sound signals (121) are detected at a sampling rate of up to 1 MHZ.

7. A system (100) for excavating dental material (107), comprising:
   a fluid jet generator (101) for generating a fluid jet (111) for excavating the dental material (107) comprising carious tooth material;
   a structure-borne sound sensor (109) for detecting structure-borne sound signals (121) of a tooth (103) generated by the fluid jet (111) during excavation; and
   a regulator or controller (105) for regulating or controlling the fluid jet generator (101) based on the structure-borne sound signals (121);
   wherein the regulator or controller (105) is configured to detect type of tooth material (107) based on the structure-borne sound signals, wherein the type of material is detected based on a slope of a cumulative energy of bursts (115) and the frequency of the bursts or the number of bursts per unit of time.

8. The system (100) according to claim 7, wherein the regulator or controller (105) is adapted to regulate or control the fluid jet generator (101) such that the fluid jet (111) is deactivated in dependence on the structure-borne sound signals (121), the fluid jet (111) is a continuous or a pulsed fluid jet (111) that is generated in dependence on the structure-borne sound signals (121), and/or a pressure of the fluid jet generation is regulated or controlled in dependence on the structure-borne sound signals (121).

9. The system (100) according to claim 7, comprising an evaluator (127) for determining and evaluating individual bursts in the structure-borne sound signals.

10. The system (100) according to claim 9, wherein the evaluator (127) has a sampling rate of up to 1 MHZ.

* * * * *